(12) United States Patent
Leijssen et al.

(10) Patent No.: US 7,714,268 B2
(45) Date of Patent: May 11, 2010

(54) DETERMINATION OF LOW CURRENTS WITH HIGH DYNAMIC RANGE FOR OPTICAL IMAGING

(75) Inventors: Jacobus Josephus Leijssen, Waalre (NL); Harry Marinus, Nuenen (NL); Martinus Bernardus Van Der Mark, Best (NL)

(73) Assignee: Koninklijke Philips Electronics N.V., Eindhoven (NL)

( * ) Notice: Subject to any disclaimer, the term of this patent is extended or adjusted under 35 U.S.C. 154(b) by 56 days.

(21) Appl. No.: 12/065,647

(22) PCT Filed: Sep. 7, 2006

(86) PCT No.: PCT/IB2006/053145

§ 371 (c)(1),
(2), (4) Date: Mar. 4, 2008

(87) PCT Pub. No.: WO2007/029191

PCT Pub. Date: Mar. 15, 2007

(65) Prior Publication Data

US 2009/0026350 A1 Jan. 29, 2009

(30) Foreign Application Priority Data

Sep. 8, 2005 (EP) .................................. 05108226

(51) Int. Cl.
*H04N 5/335* (2006.01)

(52) U.S. Cl. .............................. 250/214 R; 250/214 A; 250/208.2

(58) Field of Classification Search ............. 250/214 R, 250/214 A, 214 AG, 208.2, 232, 208.1, 332, 250/334
See application file for complete search history.

(56) References Cited

U.S. PATENT DOCUMENTS

| | | | |
|---|---|---|---|
| 5,665,959 A | 9/1997 | Fossum et al. | |
| 5,870,078 A | 2/1999 | Olyha et al. | |
| 6,150,649 A | 11/2000 | Wake et al. | |
| 6,339,216 B1 | 1/2002 | Wake | |
| 6,391,667 B1 | 5/2002 | Hashimoto | |
| 6,693,287 B2 | 2/2004 | Grable et al. | |
| 6,768,294 B1 | 7/2004 | Moldavsky et al. | |
| 2002/0044211 A1* | 4/2002 | Tujii et al. | 348/302 |
| 2002/0066850 A1* | 6/2002 | Wu et al. | 250/214 A |
| 2002/0114765 A1 | 8/2002 | Grable et al. | |
| 2003/0001080 A1 | 1/2003 | Kummaraguntla et al. | |
| 2003/0076432 A1 | 4/2003 | Luo et al. | |
| 2003/0176793 A1 | 9/2003 | Wake et al. | |
| 2004/0267488 A1 | 12/2004 | Strommer | |

* cited by examiner

*Primary Examiner*—Georgia Y Epps
*Assistant Examiner*—Tony Ko

(57) ABSTRACT

In optical tomography, a wide dynamic range is necessary while measuring currents. According to an exemplary embodiment of the present invention, the currents are measured by counting the integration time and outputting a measurement result on the basis of the counted integration time, if the integrated current exceeds a threshold value before expiration of a maximum integration time.

13 Claims, 8 Drawing Sheets

| Diode current | Integration mode | Counter if 100MHz clock is used (10ns increments) | Noise/Resolution |
|---|---|---|---|
| 1fA (< noise floor) | 10V | 1000000 counts | 35fA |
| 10fA (< noise floor) | 10uV | 1000000 counts | 35fA |
| 100fA | 100uV | 1000000 counts | 35fA |
| 1pA | 1mV | 1000000 counts | 35fA |
| 10pA | 10mV | 1000000 counts | 35fA |
| 100pA | 100mV | 1000000 counts | 35fA |
| 1nA | 1V | 1000000 counts | 35fA |
| 10nA | 10V | 1000000 counts | 35fA/0.0001% |
| 33nA | Limit reached = 10 V | 330000 counts | 0.003% |
| 100nA | Limit reached = 10 V | 100000 counts | 0.001% |
| 1uA | Limit reached = 10 V | 10000 counts | 0.01% |
| 10uA | Limit reached = 10 V | 1000 counts | 0.1% |
| 100uA | Limit reached = 10 V | 100 counts | 1% |
| 1mA | Limit reached = 10 V | 10 counts | 10% |

FIG. 5

DETERMINATION OF LOW CURRENTS WITH HIGH DYNAMIC RANGE FOR OPTICAL IMAGING

The invention relates to the field of optical imaging. In particular, the invention relates to a determination circuit for measuring a low current with a high dynamic range, to a use of the determination circuit in an optical examination apparatus, to a method of measuring a low current with a high dynamic range, a computer-readable medium and a program element.

For breast-imaging equipment, extremely low light intensities have to be measured. Determination circuits for measuring such low currents may comprise a trans-impedance amplifier which needs switching of the gain in case the currents to be measured have a wide dynamic range. Other determination circuits use current-to-voltage integrators which need a changing of the integration capacitor value or a changing of the integration time when such currents with high dynamic range have to be measured.

Furthermore, the above-described determination circuits may generate artefacts and may spend time on calibration and gain switching.

It may be desirable to have an improved determination of low currents with high dynamic range.

According to an exemplary embodiment of the present invention, a determination circuit for measuring a low current with a high dynamic range may be provided, the determination circuit comprising an integration unit and a counter unit, wherein the integration unit is adapted for integrating the current over an integration time, resulting in an integration value, wherein the counter unit is adapted for counting the integration time, resulting in a counting value, and wherein the determination circuit is adapted for outputting a first measurement result on the basis of the counting value, if the integration value exceeds a first threshold value before expiration of a maximum integration time.

Therefore, according to this exemplary embodiment of the present invention, in case a relatively high current has to be measured, the counted integration time is used for the measurement result. For example, if the integration value is higher than a first threshold value, the integration time is determined (which is the time until the integration value exceeds the first threshold value) and this integration is then used for the output.

According to another exemplary embodiment of the present invention, the determination circuit is adapted for outputting a second measurement result on the basis of the integration value, if the integration value is below the first threshold value at the expiration of the maximum integration time.

For example, in case a relatively low current is measured, the integration value will not exceed the first threshold value during the maximum (predetermined) integration time. In this case, the integration value is used in order to derive the second measurement result (which, for example, may be the integration value itself or may be proportional to the integration value. However, there may be any other dependency of the measurement result on the integration value).

According to another exemplary embodiment of the present invention, the determination circuit is adapted for outputting a third measurement result on the basis of the counting value and the integration value, if the integration value exceeds the first threshold value before the expiration of the maximum integration time and if the counting value is below a second threshold value.

According to another exemplary embodiment of the present invention, the counter unit is adapted for stopping to count when the integration value exceeds the first threshold value. Furthermore, the integration unit is adapted for stopping to integrate when the integration value exceeds the first threshold value.

Therefore, according to this exemplary embodiment of the present invention, no further counting and integrating is performed when the first threshold value has been reached. This may, for example, be performed by a stop signal which triggers stopping of the counter and stopping of the integration when the first threshold value has been reached.

According to another exemplary embodiment of the present invention, at least one of the first threshold value, the second threshold value, and the maximum integration time are predetermined by a user.

For example, according to individual measurement requirements, the user may increase the maximum integration time, for example if the measurement to be performed has to be very sensitive.

According to another exemplary embodiment of the present invention, the determination circuit further comprises an analogue-to-digital converter for converting the integration value into a digital signal.

This may provide for a digital output of the measurement result.

According to an exemplary embodiment of the present invention, if the counter did stop, for example, before the 100 ms (for example counter value 10000000) is reached, the counter value is used instead.

According to another exemplary embodiment of the present invention, the determination circuit further comprises a multiplexer adapted for multiplexing a plurality of integration values from a the integration unit, wherein the counter unit is adapted for latching a time value for each integration unit.

For example, the determination circuit may use a total of 256 channels, wherein the determination circuit comprises 16 boards with 16 channels each. On each board each of the 16 channels may measure the current from one respective diode. The resulting 16 signals are then input into one multiplexer (being a 16 channel multiplexer). Furthermore, each board may comprise one counter controller, which can latch 16 time values. The multiplexer is used to have only one ADC and one FPGA on each board of 16 channels. The total system has 16 boards that make a total of 256 channels in a machine.

According to another exemplary embodiment of the present invention, the determination circuit further comprises a clock adapted for clocking the counter unit.

According to another exemplary embodiment of the present invention, the integration unit comprises a current-to-voltage integrator adapted as a Burr Brown ACF2101 or a Burr brown IVC102.

To the end of even enhancing the noise reduction the determination circuit is isolated from the mains by capacitors C. Further, capacitors C can supply power by pulses to the determination circuit. By isolating the determination circuit the source of noise of the mains coupled thereto is eliminated, which enhances the signal to noise ratio.

Furthermore, according to another exemplary embodiment of the present invention, the above-described determination circuit is used in an optical examination apparatus for optical examination of an object of interest, the optical examination apparatus comprising an optical radiation source adapted for emitting primary optical radiation to the object of interest, a detector unit adapted for detecting radiation from the object of interest, and the determination circuit adapted for measuring a low current with a high dynamic range.

This may provide for an improved imaging for example in breast cancer diagnostics.

According to another exemplary embodiment of the present invention, a method of measuring a low current with a high dynamic range may be provided, the method comprising the steps of integrating the current over an integration time, resulting in an integration value, counting the integration time, resulting in a counting value, and outputting a first measurement result on the basis of the counting value, if the integration value exceeds a first threshold value before expiration of a maximum integration time.

It is believed that this may allow for an improved measurement of extremely low currents or light intensities using photodiodes.

According to another exemplary embodiment of the present invention, the method further comprises the steps of outputting a second measurement result on the basis of the integration value, if the integration value is below the first threshold value at the expiration of the maximum integration time, and outputting a third measurement result on the basis of the counting value and the integration value, if the integration value exceeds the first threshold value before the expiration of the maximum integration time and if the counting value is below a second threshold value.

This may provide for high dynamic range without switching and less digital feed through on low current measurements.

Furthermore, by using both, the counting value and the integration value, in case the current is relatively high (such that only a few counts have been performed until the first (integration) threshold value has been reached), the signal-to-noise ratio may further be reduced.

According to another exemplary embodiment of the present invention, the method further comprises the steps of stopping to count when the integration value exceeds the first threshold value and stopping to integrate when the integration value exceeds the first threshold value.

Furthermore, a multiplexing step may be performed in case a plurality of integration values (either from a plurality of corresponding integration units, or from one single integration unit) are measured.

According to another exemplary embodiment of the present invention, a computer-readable medium may be provided, in which a computer program of measuring a low current with a high dynamic range is stored which, when being executed by a processor, is adapted to carry out the above-mentioned method steps.

The present invention also relates to a program element of measuring a low current with a high dynamic range, which, when being executed by a processor, is adapted to carry out the above-mentioned method steps. The program element may be stored on a computer-readable medium and may be loaded into working memories of a data processor. The data processor may thus be equipped to carry out exemplary embodiments of the methods of the present invention. The computer program may be written in any suitable programming language, for example, C++ and may be stored on the computer-readable medium, such as a CD-ROM. Also, the computer program may be available from a network, such as the WorldWideWeb, from which it may be downloaded into image processing units or processors, or any suitable computers.

It may be seen as the gist of an exemplary embodiment of the present invention, that, in optical tomography, a determination of a low current with a high dynamic range is performed without gain switching or changing of integration time or integration capacitor value. According to an exemplary embodiment of the present invention, in case the integrated current exceeds a predetermined threshold value before a maximum integration time has been reached, the measurement time which has been elapsed until then is used as output. If however, the integration threshold value is not reached before expiration of the maximum integration time, the integration result is used as output.

These and other aspects of the present invention will become apparent from and elucidated with reference to the embodiments described hereinafter.

Exemplary embodiments of the present invention will be described in the following, with reference to the following drawings.

FIG. 5 shows a table representing the diode current, the integration mode, the counter and the noise/resolution according to an exemplary embodiment of the present invention.

The illustration in the drawings is schematically. In different drawings, similar or identical elements are provided with the same reference numerals.

Figure 1:
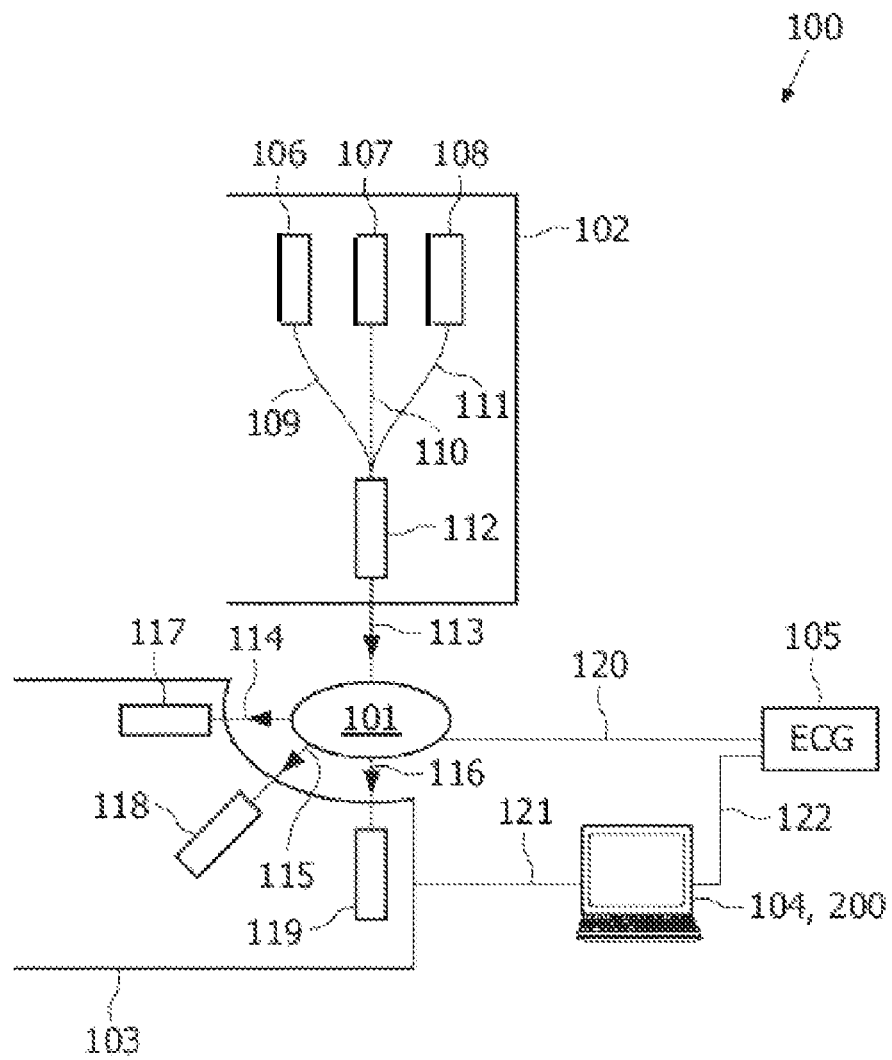
FIG. 1 shows a simplified schematic representation of an optical examination apparatus in which a determination circuit according to an exemplary embodiment of the present invention may be used.

In the following, referring to FIG. 1, an optical examination apparatus 100 comprising a determination circuit according to an exemplary embodiment of the present invention will be described in detail.

The optical examination apparatus 100 for examination of an object of interest 101, such as, for example, tissue (for example a human breast), comprises an optical radiation source 102, a detection unit 103, a determination unit 104 and as an option an electrocardiogram unit 105.

The optical radiation source 102 may comprise one or a plurality of lasers or photodiodes 106, 107, 108, each being adapted for emitting a particular wavelength. Each emitted wavelength may be an infrared near-infrared wavelength, for example between 500 nm and 1500 nm. The emitted light beams may be delivered to a coupler 112 by optical fibres 109, 110, 111. The fibre coupler 112 may be adapted for coupling the three fibres 109, 110, 111 and for emitting the combined light 113 to the object of interest 101 by direct illumination of the imaging field.

However, the examination apparatus may use more fibres as sources, for example 256 fibres, and for example 256 fibres for detection. For example, the fibres are mounted in the wall of a cup-shaped measurement chamber (for breast imaging). The source fibres are illuminated sequentially using continuous waves, and the signal of all detectors is recorded simultaneously. For example, three wavelengths may be used. However, more than three or less than three wavelengths may be used.

It should be noted, that instead of optical fibres or additionally to optical fibres 109, 110, 111, other optical elements, such as lenses (not depicted in FIG. 1) may be used for delivering the light to the object of interest 101. Furthermore, fibres, mirrors, apertures and modulators may be used for pre-processing the light. However, one single wavelength may be necessary according to an exemplary embodiment of the present invention.

The light emitted by the optical radiation source 102 impinges on the sample 101 and propagates through it. Due to the different nature of the light propagation the object of interest 101 emits transmitted radiation 114, 115, 116.

The light which is emitted from the object of interest 101 may be further processed by light collection optics (not depicted in FIG. 1), which may comprise optical elements such as lenses, mirrors and filters.

The light may be filtered in an emission filter (not depicted in FIG. 1). Any background radiation can be rejected from the collection pathway by one or a series of optical filters.

Then, the light from the object of interest 101 is detected by detector elements 117, 118, 119, which may be adapted in form of a CCD camera, photodiode, ever avalanche photodiode or a multiplier tube. According to an exemplary embodiment of the present invention, the detection signal is measured by the determination unit 200 (depicted for example in FIG. 2) and may be converted into a digital signal.

The determination unit 104 may be coupled (via line 122) to an electrocardiogram unit 105 adapted for measuring the heart cycle of the object of interest 101 via line 120. This electrocardiogram data may then be used for the elimination of motion artefacts.

The determination unit 104 may further be adapted for reconstructing a two-dimensional or a three-dimensional image of the object of interest 101 on the basis of the output of the determination circuit 200.

Figure 2:
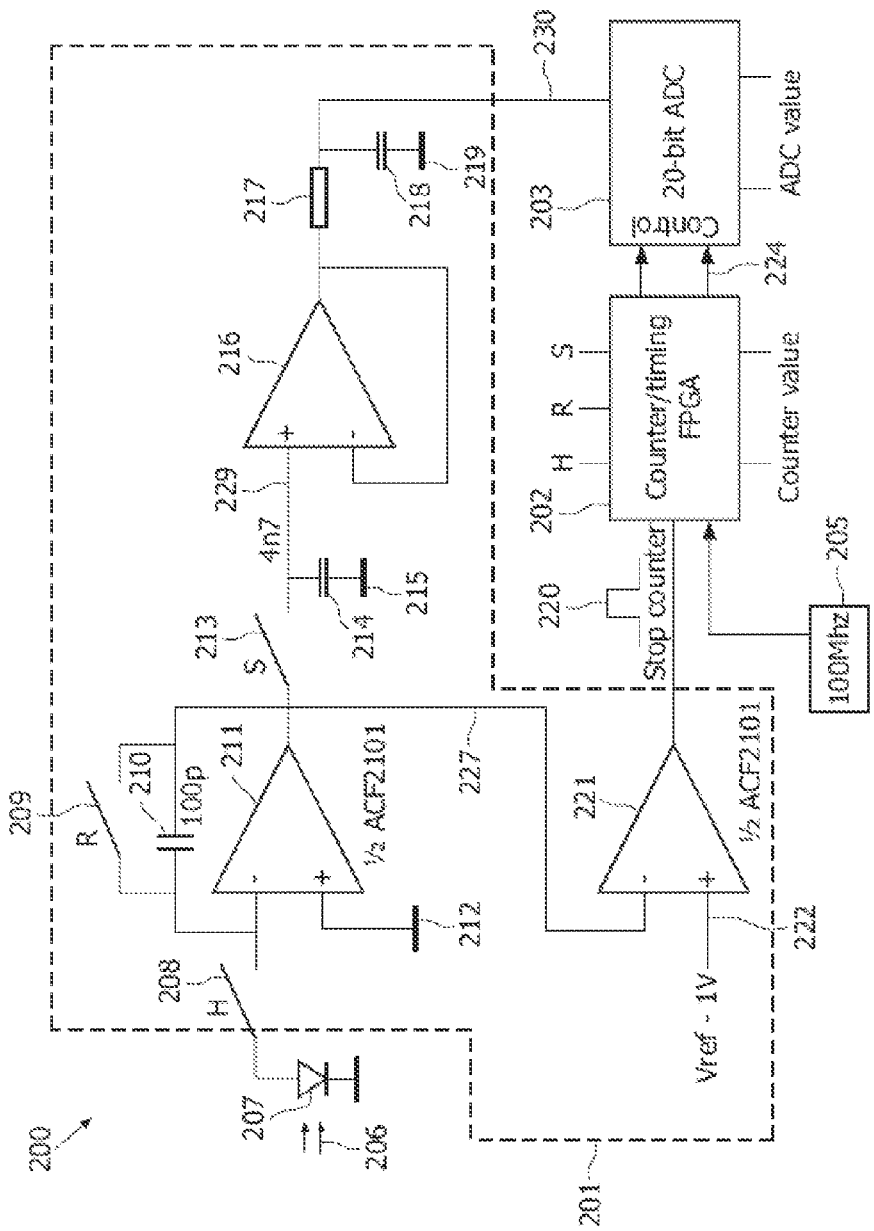
FIG. 2 shows a schematic representation of a single channel counter integrator according to an exemplary embodiment of the present invention.

FIG. 2 shows an exemplary embodiment of a single channel counter integrator or determination circuit 200 according to an exemplary embodiment of the present invention. The determination circuit 200 comprises an integration unit 201, a counter unit 202, an analogue-to-digital converter 203, for example a 20-bit analogue-to-digital converter, and a clock 205, such as a 100 MHz clock. However, different frequencies may be used for clocking.

The determination circuit 200 is adapted for measuring a low current (or a plurality of low currents) with a high dynamic range (for example a range over 12 decades) without switching, using a 20-Bit ADC (analogue-to-digital converter) 203. Alternatively, a 24-bit ADC may be used.

The currents to be measured may be generated by a photodiode 207, which detects light from a glass fibre 206.

The current is then input into the integration unit 201 over switch 208, which is connected to the counter unit 202 (which may be adapted as a counter/timing FPGA) and triggered by the "H" signal.

FPGA is a Field Programmable Gate array, a device with configurable digital logic, like counters, registers etc.

Furthermore, the integration unit 201 comprises two devices 211, 221. The first device 211 is an integration unit 211, which may be adapted as a ½ACF2101, is connected to the switch 208 at its "minus" input. The "plus" input is connected to the ground 212. Furthermore, the "minus" input is connected to capacitor 210 (which may for example have a capacity of 100 picoFarad) and (parallel to capacitor 210) switch 209 for performing a reset. Switch 209 is triggered by the "R" signal from counter unit 202.

After switch 209 and capacitor 210, the line 227 reaches the "minus" input of the second device 221, which is a comparator and which again may be adapted as a ½ACF2101.

The "plus" input of comparator 221 is connected to a reference voltage $V_{ref}$ 222, which may, for example, have the value of −1V. However, this value (which defines the first threshold value) may, according to an exemplary embodiment of the present invention, be pre-set by a user. The output of comparator 221, which generates the stop-pulse 220 to stop the integration-time counter, or latches the counter value if the counter is used for more channels, is connected to the counter unit 202 and adapted for stopping counting of the counter unit 202. The counter unit 202 is further connected to clock 205, which may be adapted as a 100 MHz oscillator.

The counter unit 202 outputs a counter value or counting value and is connected to the analogue-to-digital converter 203 via line 224. Furthermore, the counter unit 202 is adapted for outputting a hold signal "H" for controlling switch 208, a reset signal "R" for triggering switch 209 and a stop signal "S" for triggering switch 213.

Switch 213 is connected to the output of integrator 211 and, via line 229, to the "plus" input of element 216. Furthermore, line 229 is connected to capacitor 214 and then to ground 215.

The "minus" input of element 216 is connected to the output of element 216, which then leads to resistor 217 and then into the analogue-to-digital converter 203 via line 230. Line 230 is further connected to ground potential 219 via capacitor 218.

The analogue-to-digital converter 203 is adapted for outputting an ADC value, representing the integration value.

According to an exemplary embodiment of the present invention, the determination circuit 200 is adapted for outputting a first measurement result on the basis of the counting value, if the integration value exceeds the first threshold value (defined by $V_{ref}$ 222) before the expiration of a maximum integration time.

The counter 202 counts the integration time for example with 10 ns increments (100 MHz clock 205). If the integration time expires, for example after 100 ms, the ADC value is used for the measurement result output. However, on higher currents, if the output of the integrator reaches the −1V threshold, the counter value is frozen and the counter value is then used as measurement value instead of the ADC value.

In other words, if at the end of the integration cycle the counter value is lower than for example 1 million, since the integration cycle has been stopped before the expiration of the maximum integration time, the counter value must be used instead of the ADC output.

However, according to an exemplary embodiment of the present invention, if only few counts are performed before the integration threshold is reached and counting and integration are stopped, the output voltage of the integrator (or the ADC value) is used together with the counter value for measurement result determination. This may further increase the signal-to-noise ratio of the measurement.

Figure 3:
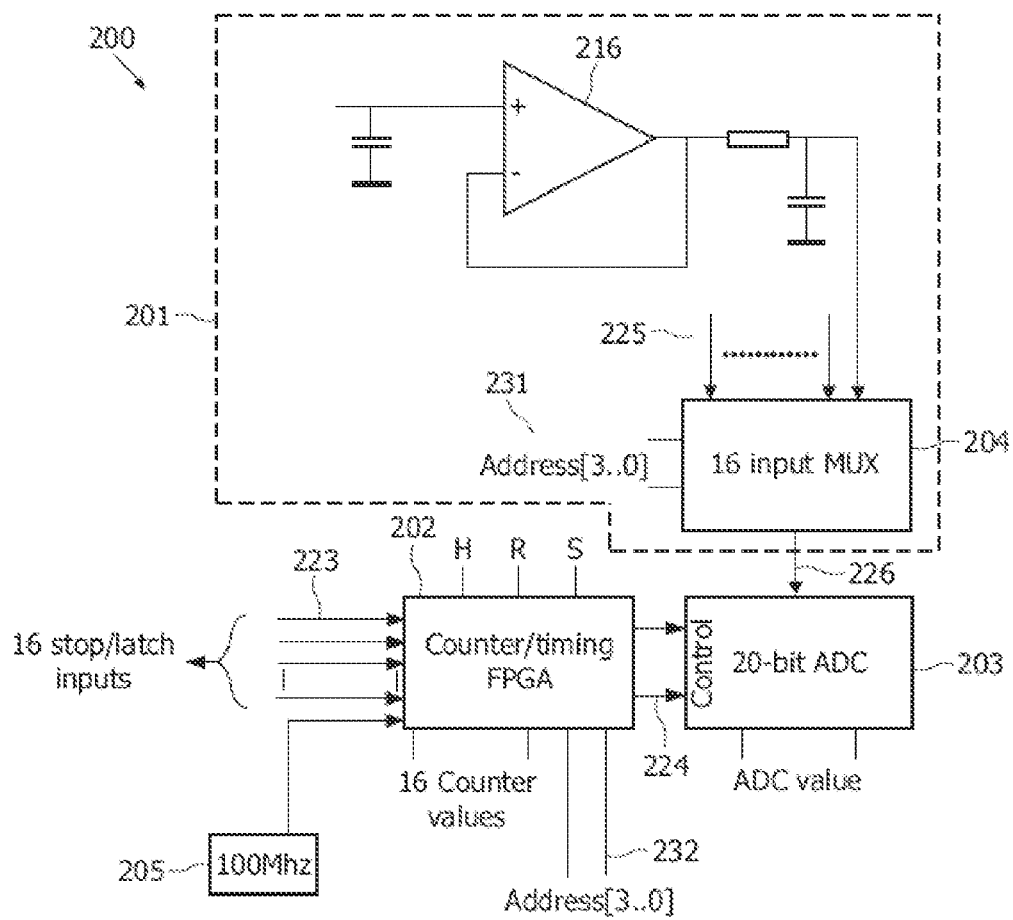
FIG. 3 shows a schematic representation of a one board configuration of 16 channels according to an exemplary embodiment of the present invention.

FIG. 3 shows a schematic representation of a one board configuration of 16 channels according to an exemplary embodiment of the present invention. As may be seen from FIG. 3, the circuit 200 further comprises a multiplexer 204 which is connected to integrator outputs 225 and adapted for multiplexing a plurality of integration values from a plurality of corresponding integration units (not depicted in FIG. 3).

Reference numeral 231 refers to a 4-bit address word to select one channel out of the 16 channels. Reference numeral 232 refers to a 4-bit address word to select one latched value out of 16 values.

Furthermore or alternatively to the multiplexer 204, the ADC 203 may be adapted as a 16 input ADC or 16 different ADCs may be provided.

Instead of using 16 counters 202, one counter 202 with 16 latches may be provided. If one of the channels generates a stop pulse the corresponding latch may be loaded with the counter's value.

The multiplexer 204, which may be adapted as a 16 channel multiplexer, is connected to the analogue-to-digital converter 203 via a line 226.

The counter unit 202 gets, as inputs, 16 stop/latch inputs 223 generated by corresponding comparators 221 (such as the one depicted in FIG. 2).

For example, a total of 256 channels are used, 16 boards with 16 channels each. On each board the ADC 203 has a 16 channel multiplexer 204 and one counter controller, which can latch 16 time values.

Figure 4:
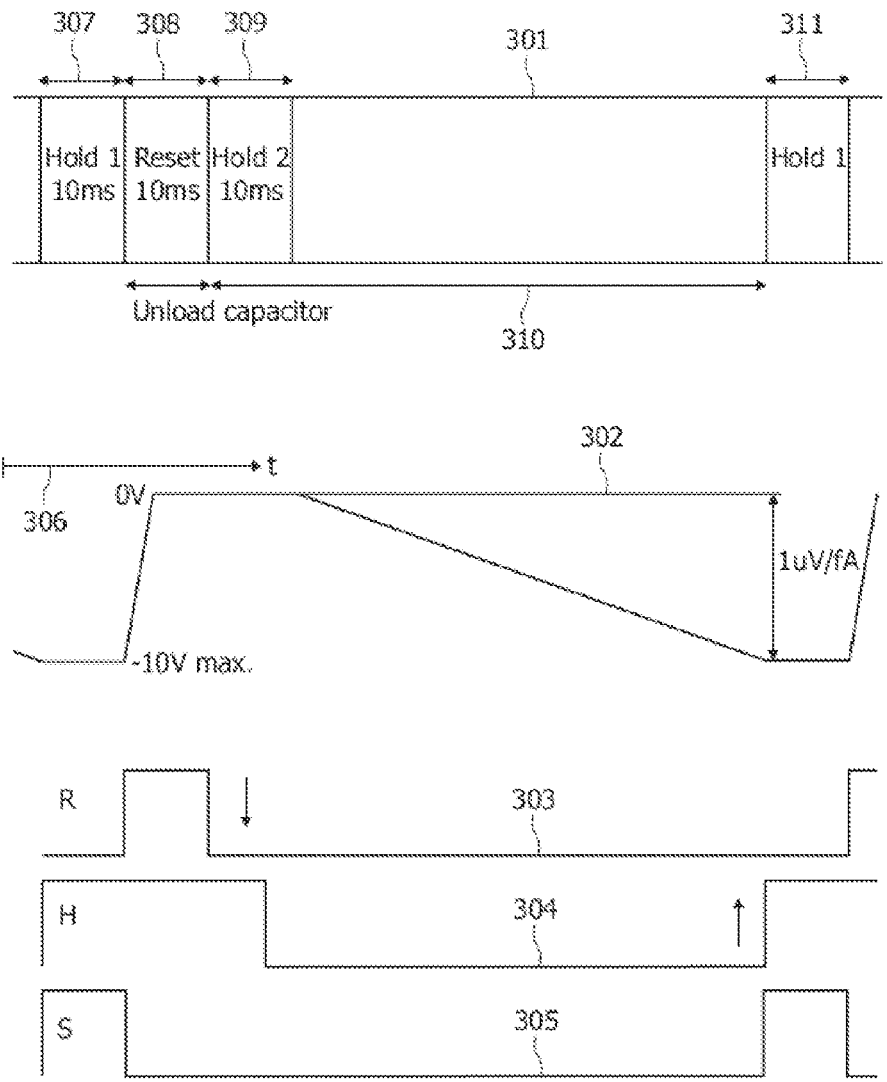
FIG. 4 shows the timing of the determination circuit according to an exemplary embodiment of the present invention.

FIG. 4 schematically depicts the timing of the determination circuit 200, comprising the counter integrator combination. The horizontal axis 306 represents the time.

As may be seen from representation 301, during a first hold 307, which for example lasts for 10 ms, a measurement and ADC averaging is performed. Then, during a reset phase 308, which is a 10 ms reset phase, the capacitor 210 is unloaded. The second hold phase 309 lasts for another 10 ms.

It should be noted however, that other time scales or phase lengths may be adapted, individually designed for respective measurement conditions.

During phase 310 the integration is performed and the capacitor 210 is loaded. This phase lasts for example for a maximum integration time of 100 ms. After that, in phase 311, a further hold is performed for measurement and ADC averaging.

Curves 303, 304 and 305 represent the R, H and S signals, respectively, which trigger the corresponding R, H, S switches 209, 208 and 213.

The counter starts on the falling edge of R 303 and stops on the rising edge of H 305 as indicated by the arrows.

Curve 302 depicts the integrator output in units μV/fA. If the integration capacitor is 100 pF and the integration time is 100 ms the integrator's output voltage is 1 μV for each femto-Ampere of photodiode current.

FIG. 5 shows a table representing the diode current, the integration mode, the counter in case of a 100 MHz clock with 10 ns increments and the noise/resolution. As may be seen from FIG. 5, the dynamic range of the determination circuit 200 is 12 decades (from 1 fA to 1 mA). Furthermore, for the value 10 nA, both measurement modes (integration and counting) are valid.

According to an exemplary embodiment of the present invention, time-consuming gain switching and waiting to be settled, may be skipped. The throughput of a single breast measurement may be reduced to the half. Instead of time reduction it is possible to do a measurement with more laser colours, for example 6 instead of 3. This may result in a better image quality of the picture, better diagnostics, without enlarging the patient's measurement time. Furthermore, with this new principle, the efficiency of the photons measured, the so-called quantum efficiency, may be higher.

Particular advantages of the determination circuit 200 according to the present invention may be that 12 decades dynamic range (40-bits) without switching may be measured using a 20-bits ADC. Furthermore, a measurement may provide for a low bandwidth for data transfer to the PC (only an ADC voltage and the counter value 64×256×256×6=25.2 Megabit/153 seconds=165 K/sec. Furthermore, the invention may provide for a reduced digital feed through on low current measurement and no digital switching or control signals during integration. This may result in a high signal-to-noise ratio.

Still further, the determination circuit 200 may make isolation of digital analogue worlds easier and may provide for an improved long-term stability than trans-impedance amplifiers, which use Giga Ohm resistors to obtain the gain. Furthermore, there may be no short and long-term drift.

Since no digital switches into the integrator are used on low currents, no (MicroCoulomb) noise may be generated. No switching may be performed on low currents until the 100 ms at depression times expires. Accordingly, the noise may be reduced compared to the method of adding many short samples.

According to the present invention, the integrator is used as a current to voltage converter for low currents. For higher currents, the counter stop (latch) method is used.

Figure 6:
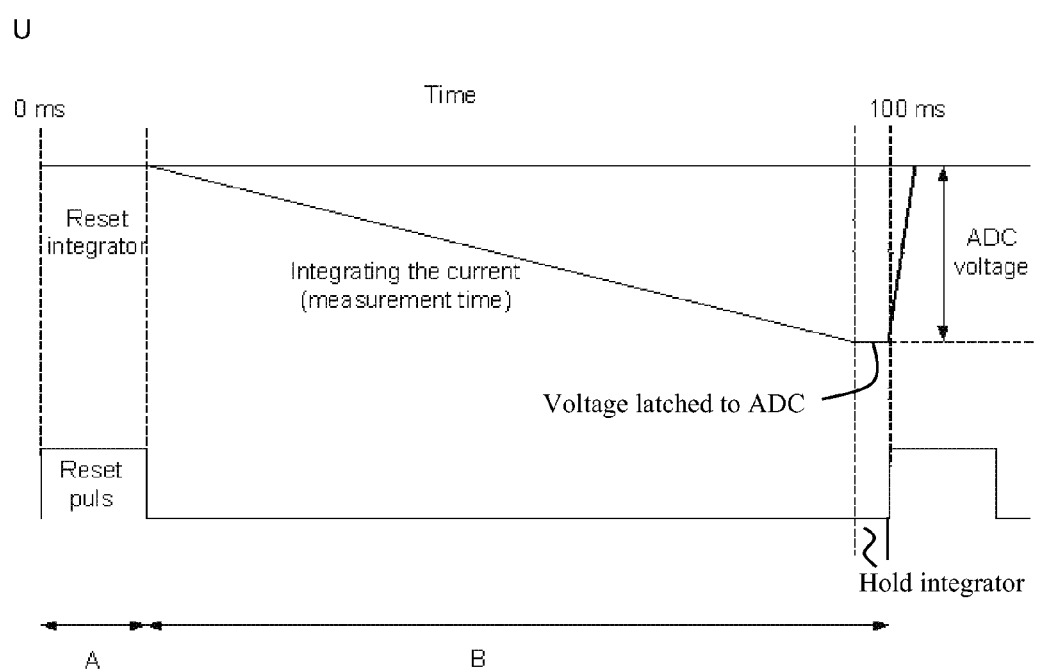
FIG. 6 shows a timing diagram of a current integrator using capacitors as a power supply.

FIG. 6 shows a timing diagram of a current integrator using capacitors as a power supply, whereby at the horizontal axis the time is plotted and at the perpendicular axis the voltage U is plotted. Shown is one integration cycle starting with a reset pulse lasting for the time A. During time A in FIG. 6 noise occurs, which occurs when resetting the integrator 211 and loading the capacitors 210, 214, 218. Also, the digital data is transferred from the determination circuit 200 to the data acquisition system. During time B in FIG. 6 the system is isolated from the mains. Then, the capacitors 210, 214, 218 supply the determination circuit 200 with energy. All digital processing must be minimized during integration time, when the current is integrated, due to the fact that the system is very sensitive for noise then. Integration time is shown in FIG. 6 at the sloping ramp after resetting and lasts until the integrator 211 is stopped. Thereafter, a constant curve is shown when the voltage is latched to the ADC 203. At the end of the hold time having a constant voltage another reset pulse is transmitted which starts another integration cycle.

Figure 7:
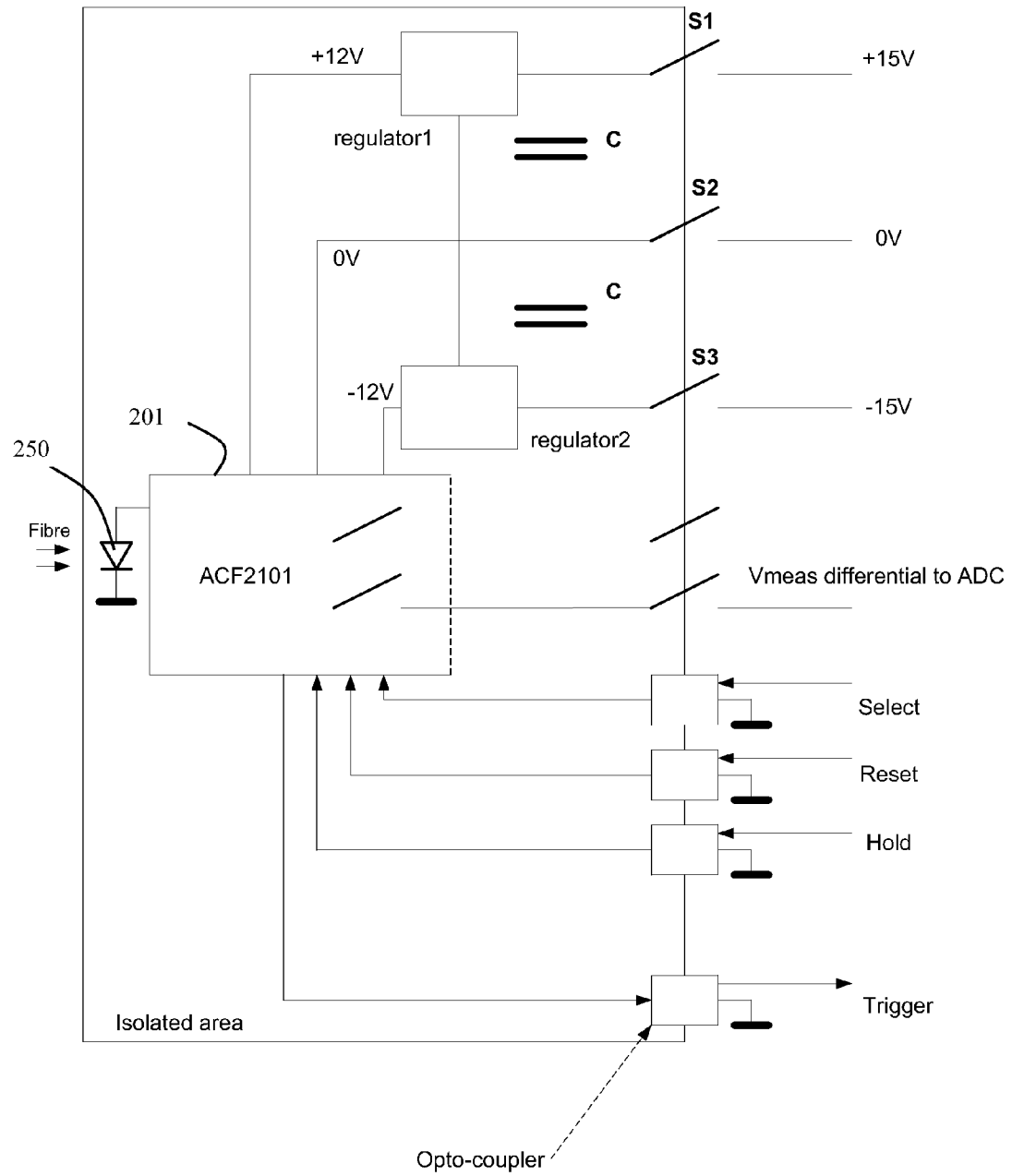
FIG. 7 shows a block diagram of a circuit using capacitors as a power supply according to FIG. 6.

FIG. 7 shows an example of a block diagram of how the isolation with capacitors C can be implemented. Shown is a part of the determination circuit 200 comprising the integration unit 201, mains at the right side of FIG. 7, and data lines. The capacitors C are loaded during the time of the reset pulse of the integration cycle as shown in FIG. 6, denoted with the term reset integrator. Regulators, denoted as regulator1, regulator2, if necessary could compensate the voltage drooping of the capacitors C during the integration cycle. The determination circuit 200 is built by example comprising a photo diode 250 as a receiver of optical data to be measured in such a way that it can be isolated with switches S1, S2, S3. The switches S1, S2, S3 can be designed mechanical or electronic, for example by CMOS, transistor or field-effect transistor. The ADC can have internal switches meant for multiplexing which can be used for isolation. Such an ADC is for example available as Texas Instruments (Burr & Brown) ADS 1256. All other digital and analogue signals must be isolated as well. For isolating the digital signals opto-couplers can be used. The switches S1, S2, S3 can be made from silicon which have a high isolation value of 100 Giga Ohms or more. The remaining capacitance of the capacitors C can have a low value in this case.

The capacitors C are used as a short-term battery as power supply in a switched mode. At certain times those capacitors C will be loaded with energy. This loading time of the capacitors C can be much shorter than the unloading time of the capacitors C. Loading of the capacitors C can be done with a short peak current. The electronic components of the determination circuit 200 can be supplied a much longer time than the time duration of the short peak current. A practical ratio of loading to unloading time can be 1:5 or 1:10. The sensitive current integrators are supplied with the loaded capacitor voltage for 50-100 ms within the integrating time of the capacitors C. During the integrator reset time A (for instance 10 ms) the digital data stream is transferred to a host computer for data acquisition. During this time the capacitors C can be loaded. The next cycle having a time of 50 or 100 ms can be measured while the capacitors C are again loaded and the digital busses are quiet and do not transfer any data. During the measurement time, which is the integration active time characterized by the slope in FIG. 6, the determination circuit 200 is isolated from the mains. By this measure described no disturbance of the measurement of low currents will occur.

Figure 8:
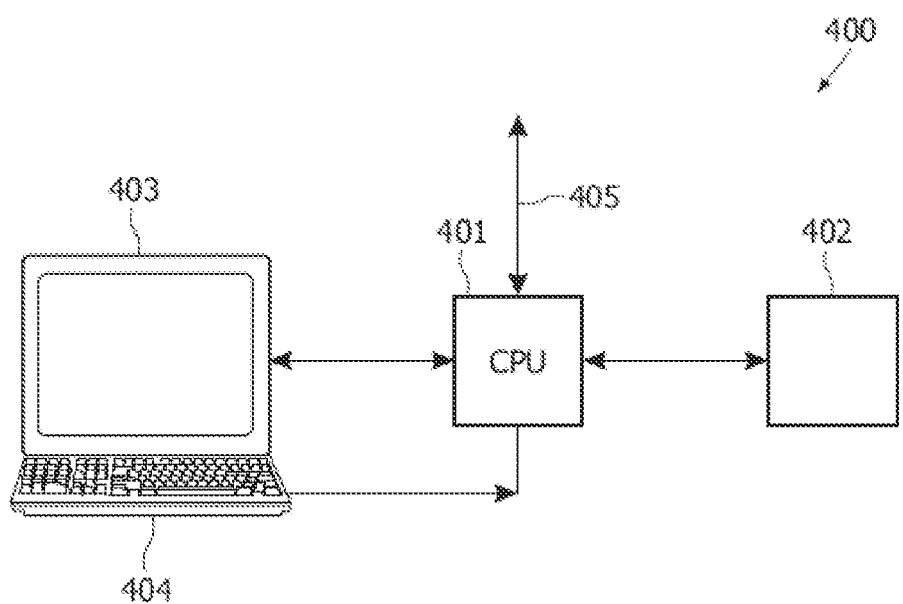
FIG. 8 shows an exemplary embodiment of a processor according to the present invention for executing an exemplary embodiment of a method in accordance with the present invention.

FIG. 8 shows an exemplary embodiment of a processor 401 for executing an exemplary embodiment of the method in accordance with the present invention.

The processing device 400 depicted in FIG. 8 comprises the processor 401 connected to a memory 402 for storing an image depicting an object of interest, such as a breast or other piece of tissue. The data processor 401 may be connected to a plurality of input/output devices, such as an optical tomography device and may be integrated for example in counter unit 202 (depicted in FIG. 2). The data processor 401 may furthermore be connected to a display device 403, for example, a computer monitor, for displaying information or image computed or adapted in the data processor 401. An operator or user may interact with the data processor 401 via a keyboard 404 and/or other output devices, which are not depicted in FIG. 8.

Furthermore, via the bus system 405, it may also be possible to connect the processor 401 to, for example, a motion monitor, which monitors a motion of the object of interest. For example, the motion sensor may be an exhalation sensor or electrocardiogram unit.

Exemplary embodiments of the invention may be sold as a software option to imaging workstations.

It should be noted that the term "comprising" does not exclude other elements or steps and the "a" or "an" does not exclude a plurality and that a single processor or system may fulfil the functions of several means of a unit recited in the claims. Also elements described in association with different embodiments may be combined.

It should also be noted, that any reference signs in the claims shall not be construed as limiting the scope of the claims.

The invention claimed is:

1. A determination circuit for measuring a low current with a high dynamic range, the determination circuit comprising:
   an integration unit adapted for to integrate the current over an integration time, resulting in an integration value;
   a counter unit to count the integration time, resulting in a counting value;
   wherein the determination circuit is adapted to: output a first measurement result on the basis of the counting value, if the integration value exceeds a first threshold value before expiration of a maximum integration time; and to output a third measurement result on the basis of the counting value and the integration value, if the integration value exceeds the first threshold value before the expiration of the maximum integration time and if the counting value is below a second threshold value.

2. The determination circuit of claim 1, wherein the determination circuit is adapted for outputting a second measurement result on the basis of the integration value, if the integration value is below the first threshold value at the expiration of the maximum integration time.

3. The determination circuit of claim 1, wherein the counter unit is adapted to stop counting when the integration value exceeds the first threshold value; and wherein the integration unit is adapted for stopping to integrate when the integration value exceeds the first threshold value.

4. The determination circuit of claim 1, wherein at least one of the first threshold value, the second threshold value, and the maximum integration time are predetermined by a user.

5. The determination circuit of claim 1, further comprising: an analogue-to-digital converter for converting the integration value into a digital signal.

6. The determination circuit of claim 1, further comprising: a multiplexer (204) adapted for multiplexing a plurality of integration values from the integration unit; wherein the counter unit is adapted for latching a time value for each integration unit.

7. The determination circuit of claim 1, further comprising: a clock adapted for clocking the counter unit.

8. The determination circuit of claim 1, wherein the integration unit comprises at least one of a current-to-voltage integrator adapted as a Burr Brown ACF2101 and a Burr Brown IVC102.

9. The determination circuit of claim 1, wherein the determination circuit is isolated from a mains by capacitors C which supply power by pulses to the determination circuit.

10. Use of a determination circuit of claim 1 in an optical examination apparatus for optical examination of an object of interest, the optical examination apparatus comprising: an optical radiation source adapted for emitting primary optical radiation to the object of interest; a detector unit adapted for detecting radiation from the object of interest; a determination circuit of claim 1 adapted for measuring a low current with a high dynamic range.

11. A method of measuring a low current with a high dynamic range, the method comprising:
   integrating the current over an integration time, resulting in an integration value;
   counting the integration time, resulting in a counting value;
   outputting a first measurement result on the basis of the counting value, if the integration value exceeds a first threshold value before expiration of a maximum integration time;
   outputting a second measurement result on the basis of the integration value, if the integration value is below the first threshold value at the expiration of the maximum integration time; and
   outputting a third measurement result on the basis of the counting value and the integration value, if the integration value exceeds the first threshold value before the expiration of the maximum integration time and if the counting value is below a second threshold value.

12. The method of claim 11, further comprising:
   stopping counting when the integration value exceeds the first threshold value;
   and stopping integrating when the integration value exceeds the first threshold value.

13. The method of claim 11, further comprising:
   integrating a second current over a second integration time, resulting in a second integration value; and
   multiplexing a plurality of integration values from the integration unit; latching a time value for each integration unit.

* * * * *